United States Patent
Lindh, Sr. et al.

(10) Patent No.: US 8,101,116 B2
(45) Date of Patent: Jan. 24, 2012

(54) PREFORMED SUPPORT DEVICE AND METHOD AND APPARATUS FOR MANUFACTURING THE SAME

(75) Inventors: David C. Lindh, Sr., Flemington, NJ (US); Etan S. Chatlynne, Brooklyn, NY (US)

(73) Assignee: Ethicon, Inc., Somerville, NJ (US)

( * ) Notice: Subject to any disclaimer, the term of this patent is extended or adjusted under 35 U.S.C. 154(b) by 323 days.

(21) Appl. No.: 12/234,026

(22) Filed: Sep. 19, 2008

(65) Prior Publication Data

US 2009/0240342 A1    Sep. 24, 2009

Related U.S. Application Data

(60) Provisional application No. 61/097,677, filed on Sep. 17, 2008, provisional application No. 60/994,433, filed on Sep. 19, 2007.

(51) Int. Cl.
*B29C 43/02* (2006.01)

(52) U.S. Cl. ........ 264/550; 264/544; 264/549; 264/554; 264/324; 425/358; 425/412

(58) Field of Classification Search .................. 264/320, 264/323, 324, 544, 549, 550, 554; 425/330, 425/344, 346, 356, 357, 358, 389, 412
See application file for complete search history.

(56) References Cited

U.S. PATENT DOCUMENTS

| | | | |
|---|---|---|---|
| 4,008,029 A | 2/1977 | Shokite | |
| 4,428,375 A | 1/1984 | Ellman | |
| 4,481,951 A * | 11/1984 | Cole et al. | ........................ 450/20 |
| 5,954,767 A | 9/1999 | Pajotin et al. | |
| 6,241,768 B1 | 6/2001 | Agarwal et al. | |
| 6,416,459 B1 * | 7/2002 | Haindl | ............................ 600/37 |
| 6,723,133 B1 | 4/2004 | Pajotin | |
| 6,951,534 B2 | 10/2005 | Girard et al. | |
| 2005/0051923 A1 | 3/2005 | Warren | |
| 2006/0030939 A1 | 2/2006 | Frank | |

FOREIGN PATENT DOCUMENTS

WO  WO 2004/096098 A1  11/2004
WO  WO 2007/004214 A    1/2007

* cited by examiner

*Primary Examiner* — Joseph Del Sole
*Assistant Examiner* — Timothy Kennedy

(57) ABSTRACT

A device for making a seamless, anatomically contoured, prosthetic device for supporting or maintaining the position of mammalian tissue, organ or structure or a replacement thereof, such as a breast implant, includes a support plate, an ironing plate or a clamping plate and a core plate, each of which is made from a thermally conductive material. The support plate and the ironing or clamping plates have openings formed through the thickness thereof. The core plate has a core extending outwardly from a lower surface thereof which is received through the openings in the ironing or clamping plate and the support plate.

6 Claims, 12 Drawing Sheets

PREFORMED SUPPORT DEVICE AND METHOD AND APPARATUS FOR MANUFACTURING THE SAME

CROSS-REFERENCE TO RELATED APPLICATIONS

This application claims the benefit of U.S. Provisional Application Ser. No. 61/097,677, filed on Sep. 17, 2008 and U.S. Provisional Application Ser. No. 60/994,433, filed on Sep. 19, 2007.

BACKGROUND OF THE INVENTION

1. Field of the Invention

The present invention relates generally to prosthetic devices for supporting or maintaining the position of mammalian tissue and the like and replacements therefor, and more particularly relates to a method and apparatus for manufacturing such prosthetic devices.

2. Description of the Prior Art

Surgical meshes are an example of a support device for supporting or reinforcing tissue or muscle, or supporting and/or maintaining the position of natural anatomical structures (e.g. spleens or breast tissue), or certain anatomical replacements (e.g. breast implants).

In the case of supporting and maintaining the position of breast implants, some surgeons cut flat, two dimensional meshes to the desired size and shape creating a formed support device, and then sew them to the desired form during surgery while in the sterile field. Examples of such techniques are described in U.S. Patent Application Publication No. 2006/0030939 having Robert E. Frank as the named inventor, and PCT Patent Application Publication No. 2004/096098 having Jonathan Hamilton, et al. as the named inventors. This activity carries two primary disadvantages. First, cutting the mesh in an operating room creates fine (albeit sterile) dust, a byproduct that is undesirable to have in a clean operating room. Second, and perhaps more importantly, the preparation of a flat mesh into a formed support device takes time and energy; it is well established that minimizing the length of time of a given surgical procedure is a health and cost benefit to all.

In the case of supporting and maintaining the position of other anatomical structures or replacements, such as a spleen or heart, some surgeons use mesh bags, as described in U.S. Pat. No. 4,428,375, which issued to Barry R. Ellman. These mesh bags may be likened to purse strings used to cinch the mesh bag around the structure or the replacement. The final configuration of the mesh bag conforms to the structure it supports, but often has wrinkles and folds. These wrinkles and folds define areas where the support has varied across locations. At the folds and wrinkles, the support is minimal. Furthermore, the wrinkles and folds define areas of increased surface area where adhesions may form and can cause the mesh to migrate, concomitantly causing the mesh to pull on the structure whose position the mesh is meant to maintain. Furthermore, adhesions are known causes of post-surgical pain. The term "wrinkles and folds" used herein connotes any wrinkles, folds, pleats, or the like and any combination thereof that may form in a mesh while the mesh is being used in a surgical procedure.

Some support devices are cumbersome to apply when they do not possess a sufficient resiliency or stiffness property. The shape of such devices, lacking the ability to support their own weight without collapsing, must be manually maintained in order to position the support device and to secure it in place. For example, a mesh knitted as a three dimensional shape made from conventionally sized medical mesh polypropylene fibers will collapse under its own weight. When used in a surgery, this effect is exacerbated as the mesh becomes sullied with blood and other body fluids.

Some patents or published patent applications describe preformed meshes for repairing hernias (i.e. for reinforcing tissue and muscle). These preformed meshes are significantly smaller and have a much less significant preform than a formed support device used for supporting an anatomical structure or replacement. Creating a preformed support device suitable for supporting natural breast tissue or a breast implant using the methods described in the hernia mesh patents or published patent applications may impart pleats or folds into the preformed support device. The presence of pleats and folds creates excess foreign body that is placed into a human body during the surgical procedure which may attribute to serious side effects such as infection and scar formation. Therefore, it is desirable to minimize the amount of foreign body introduced into the body by eliminating any pleats or folds. The term "pleats or folds" connotes any wrinkles, folds, pleats, or the like or any combination thereof that may form in a sheet of material while it is being shaped into a preformed support device.

Anatomical structures and replacements are subject to dynamic loading over a wide array of loading conditions for varied periods of time. For example, conventionally, the mesh bag used to support a spleen is absorbable, while a mesh sheet used for supporting a breast implant is non-absorbable. The support device must be strong and resilient enough to autonomously maintain its form and structure, and additionally the position of the structure or replacement.

U.S. Patent Application Publication No. 2006/0030939 of Frank and PCT Patent Application Publication No. 2004/096098 of Hamilton, et al. describe formed support devices for natural breast tissue and breast implants. The Frank and Hamilton, et al. published applications both describe two dimensional shapes precut into a mesh to facilitate the process of making a formed support device during surgery. However, neither published application describes the creation of a preformed support device.

U.S. Pat. No. 5,954,767, which issued to Philippe Pajotin, et al., and U.S. Pat. No. 6,723,133, which issued to Philippe Pajotin, both describe a preformed curved mesh. Both patents describe meshes having a permanent three dimensional shape formed via a thermoforming process. The specific thermoforming process for forming the mesh described in these patents is not adequate to create a preformed support device capable of supporting a breast implant or natural breast tissue (or other anatomical structure or structural replacement) for long periods of time. The processes disclosed in the Pajotin et al. and Pajotin patents could impart folds or pleats into a preformed support device having a large surface area to cavity opening area ratio. Notably, the processes described in these patents suggest placing the mesh in the mold prior to heating the mesh or the molds. Furthermore, the process disclosed in the '133 Pajotin patent imparts a permanent shape to a mesh by annealing and shrinking (over some, but not all, of the disclosed temperature range). In the manner described in these patents, there is little if any control over the strength and resiliency properties of the mesh. When the mesh is only annealed, its fibers become weaker. When the mesh is annealed and shrunk, the fibers become thicker and the distance between the wales is lessened. It is unclear which process conditions yield a stronger or weaker final mesh. As a point of clarification, the title of the '133 Pajotin patent is "Preformed Curved Prosthesis Having a Reduced Incidence of Developing Wrinkles or Folds." It is noted that these wrinkles and folds are those that may be introduced to the mesh while the mesh is being used in a surgical procedure. These "wrinkles and folds" are different from the pleats and folds described in the present invention. These pleats and folds refer specifically to those pleats and folds that may be formed during the fabrication process of the preformed support device.

U.S. Pat. No. 6,241,768, which issued to Vishvaroop Agarwal, et al., describes a prosthetic device for repairing hernias that is also formed from a mesh. This device has a preformed curved feature that is formed via a thermoforming process. The forming process and its shortcomings are similar to those described for the '133 Pajotin patent and the '767 Pajotin, et al. patent. It is not clear from the description whether or not the mold is heated before or after the mesh is introduced to it.

Some have attempted to use formed mesh bags. U.S. Pat. No. 4,428,375 to Ellman, is an example of a tubular mesh bag used for supporting a spleen. U.S. Pat. No. 6,951,534, which issued to Michael J. Girard et al., discloses an example of a cardiac wrap. Bags that are created from fabric sheets, like Ellman's, have conventionally been formed using additional materials (e.g. an additional stitch to maintain the configuration of the bag). Existing mesh bags that have been knitted into complex shapes directly, like Girard's, are created by a knitting process. These bags are knitted into the desired configuration, a task accomplished only with very complicated and expensive equipment or by hand.

OBJECTS AND SUMMARY OF THE INVENTION

It is an object of the present invention to provide a preformed support device that conforms to an anatomical structure or replacement without wrinkles and folds.

It is another object of the present invention to provide a preformed support device that obviates the creation of dust and removes the need to create a formed support device during a procedure.

It is still another object of the present invention to provide a method and apparatus for manufacturing a preformed support device that is entirely free of pleats or folds.

It is a further object of the present invention to provide a preformed support device that can support tensile loads that are substantially similar to the tensile loads that conventional preformed devices can support.

It is yet a further object of the present invention to provide a preformed support device that is as resilient as the preformed device.

It is another object of the present invention to improve the standard of care for supporting and/or maintaining the position of natural anatomical structures and anatomical replacements using a manufactured mesh that conforms to the selected structure or replacement more readily than the flat mesh of the conventional designs.

A method and apparatus for manufacturing a prosthetic device for supporting or maintaining the position of mammalian tissue, structures, organs or manufactured replacements therefor, and such a prosthetic device formed in accordance with the present invention, are disclosed. The device formed in accordance with the method and apparatus of the present invention has a preformed, three dimensional shape, for conforming to an anatomical structure or replacement for the purpose of supporting it and/or maintaining its position within a body.

The materials utilized in the manufacture of known preformed support devices are either weaker or less resilient than the original material from which they are made or have a larger cross sectional area. The preformed support device formed by the method and using the apparatus of the present invention has relatively invariant strength, resiliency and cross sectional area properties throughout manufacturing and processing. The resiliency of the device formed by the method and apparatus of the present invention as a whole is capable of supporting minimally its own weight and additionally can support the weight of adhering body fluids, independent of the size of the device.

While preformed meshes are conventionally known in the art, the preformed support device constructed in accordance with the method and apparatus of the present invention is unique by dimensional ratio. The forming process of the present invention yields preformed mesh devices having a significantly larger surface area to cavity opening area ratios than the preformed mesh devices of conventional design. Key embodiments of the present invention ensure that the preformed support device can be made to have the desired surface area ratio while also having a smooth surface, free from pleats and folds. The conventional manufacturing methods of performing meshes are not capable of producing a preformed mesh exhibiting the unique, desirable properties of the mesh prosthesis formed by the method and using the apparatus of the present invention.

According to one embodiment, the apparatus of the present invention includes ironing components and features. In combination, these components and features allow for the formation of a preformed support device having the unique properties described above. In another embodiment, a separate clamping component or clamping plate is used in lieu of the heated ironing component.

Another unique property of the manufacturing process of the present invention is that the original mesh is preferably shrunk before it is formed by stretching. The shrinking and stretching steps are preferred in order to create a preformed support device having the unique features described above.

Apparatus for making a seamless, anatomically contoured, preformed prosthetic device for supporting or maintaining the position of mammalian tissue, organ or structure or a replacement therefor, such as a breast implant, includes a support plate, an ironing plate or clamping component, and a core plate. Each of the support plate, ironing plate or clamping component, and core plate are preferably made from a thermally conductive material so that the plates may be heated during the manufacturing process.

The support plate includes a first opening formed through the thickness thereof, the first opening having a predetermined shape. The ironing plate or clamping plate has a second opening formed through the thickness thereof, the second opening having a predetermined shape which is either the same as or similar to the predetermined shape of the first opening formed in the support plate.

The core plate has a lower surface and a core extending outwardly from the lower surface thereof. The core has a predetermined male form, and is at least partially receivable by and extendible through the second opening of the ironing plate or clamping plate and the first opening of the support plate.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

Figure 1:
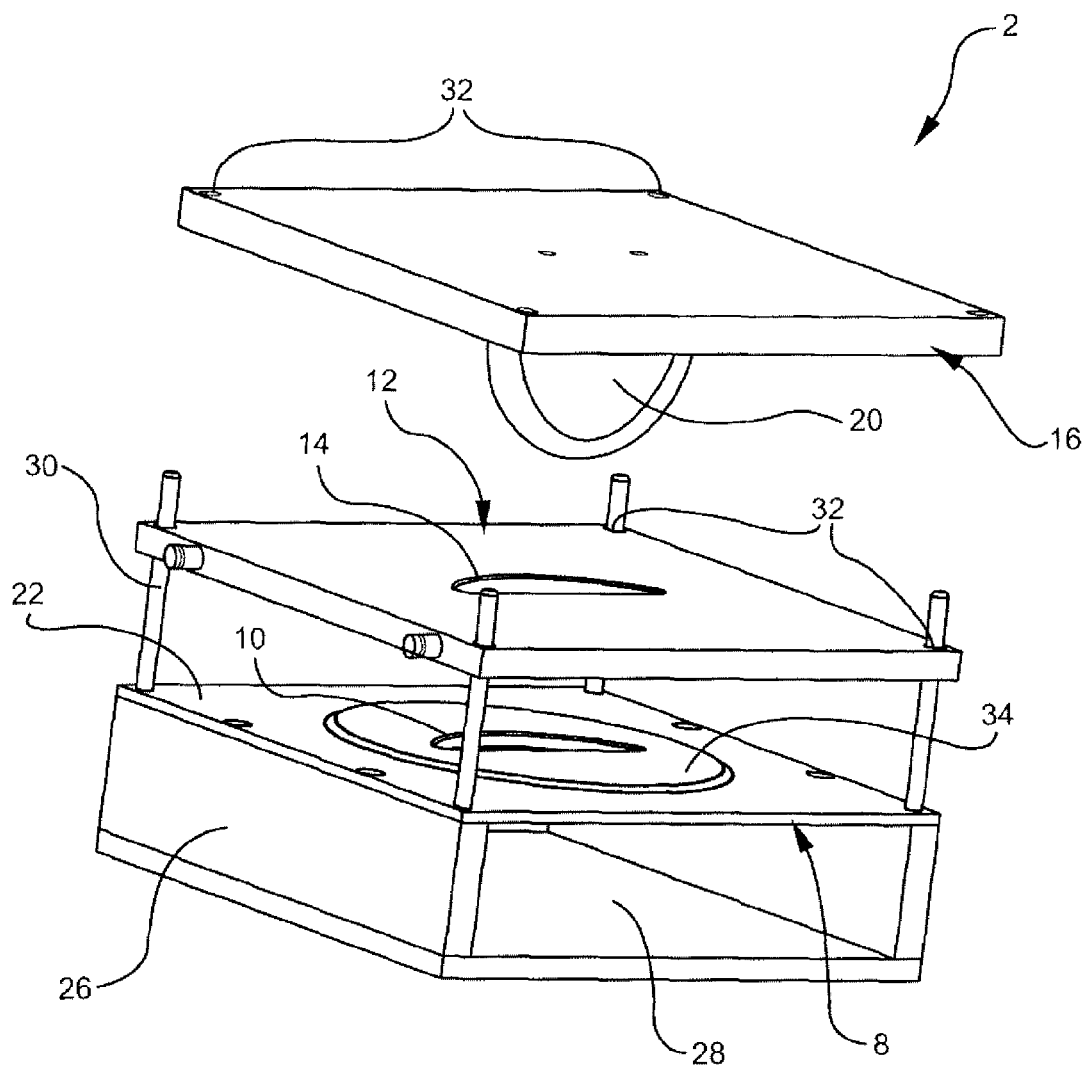
FIG. 1 is a semi-exploded, top isometric view of apparatus formed in accordance with the present invention for manufacturing a seamless, anatomically contoured, prosthetic device for supporting an anatomical structure or replacement therefor.
Figure 2:
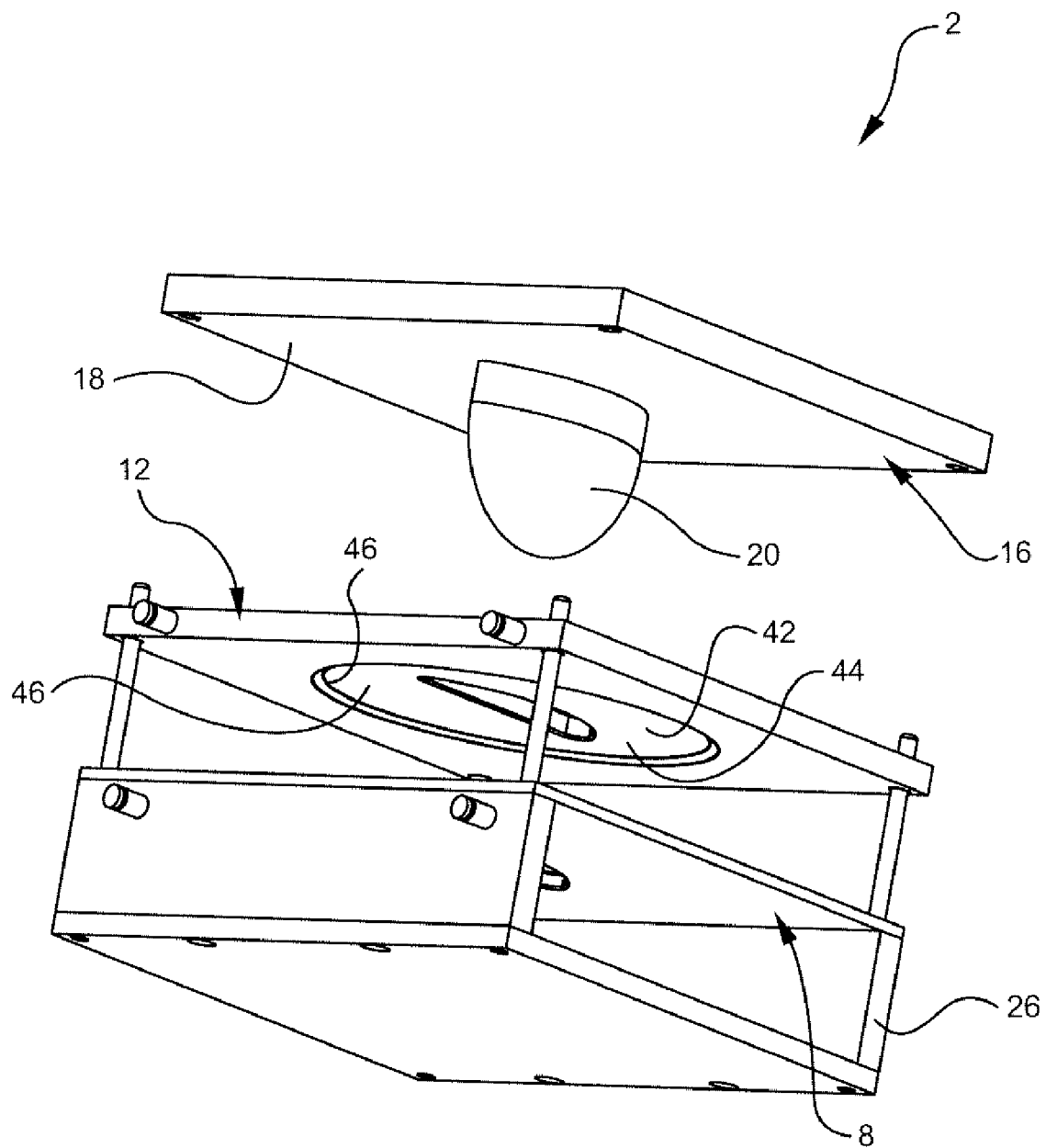
FIG. 2 is a semi-exploded, bottom isometric view of the apparatus shown in FIG. 1 formed in accordance with the present invention for manufacturing a prosthetic device.
Figure 3:
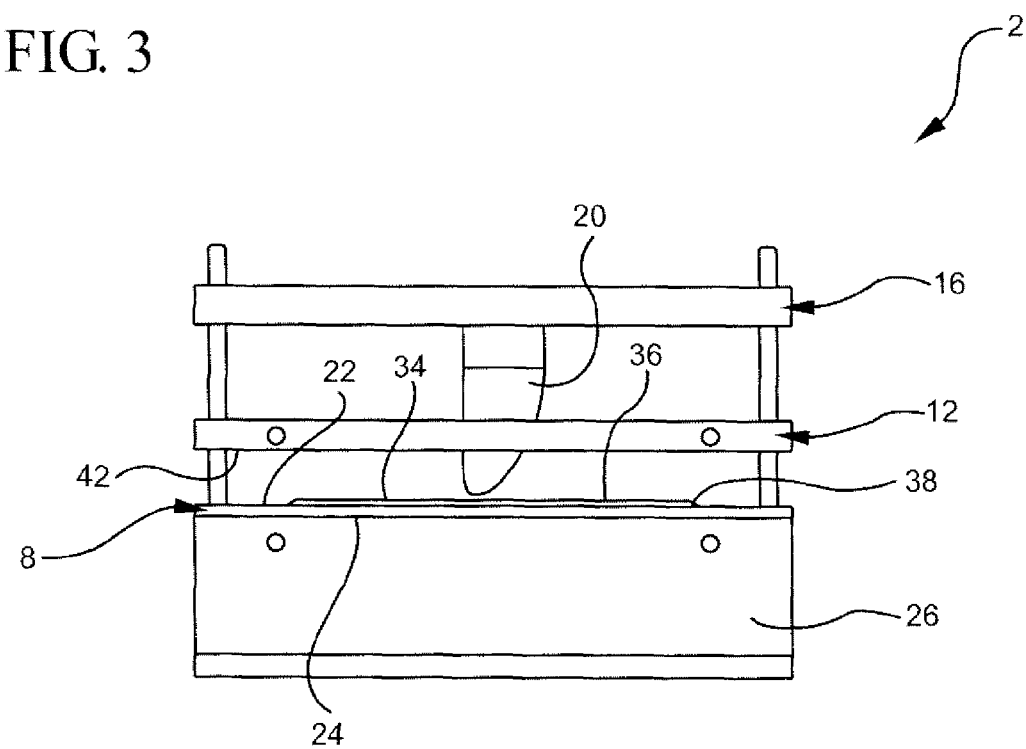
FIG. 3 is a side view of the prosthesis forming apparatus shown in FIGS. 1 and 2 constructed in accordance with the present invention and illustrated in the open configuration, prior to the prosthetic device being formed.
Figure 4:
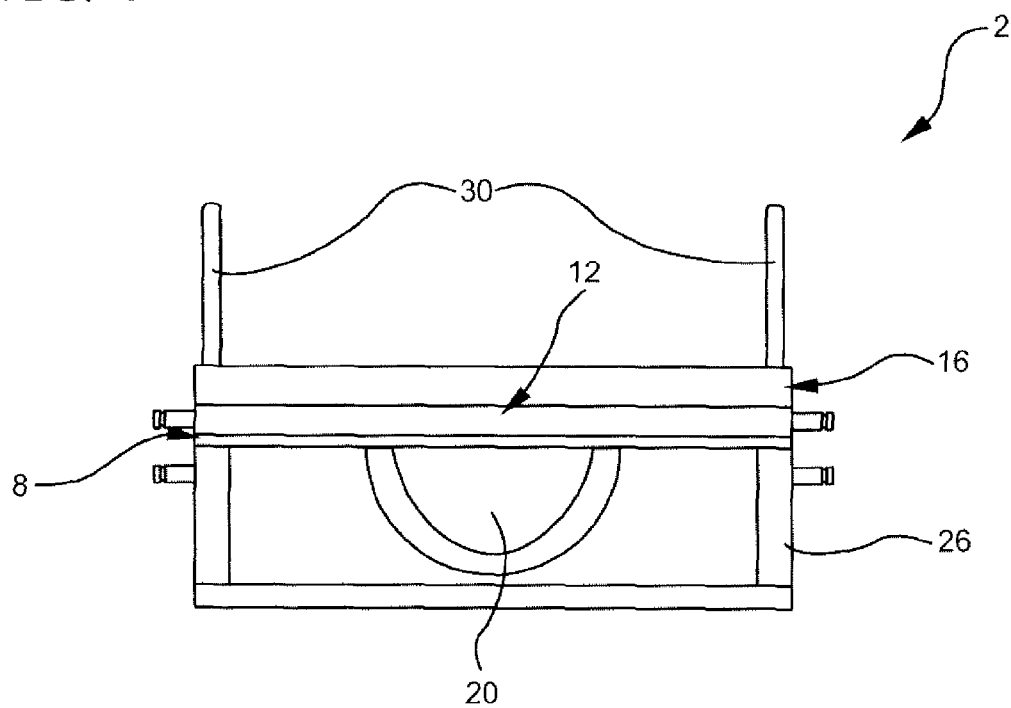
FIG. 4 is a front view of the prosthesis forming apparatus of the present invention shown in FIGS. 1-3, illustrating the apparatus in a closed configuration.
Figure 5:
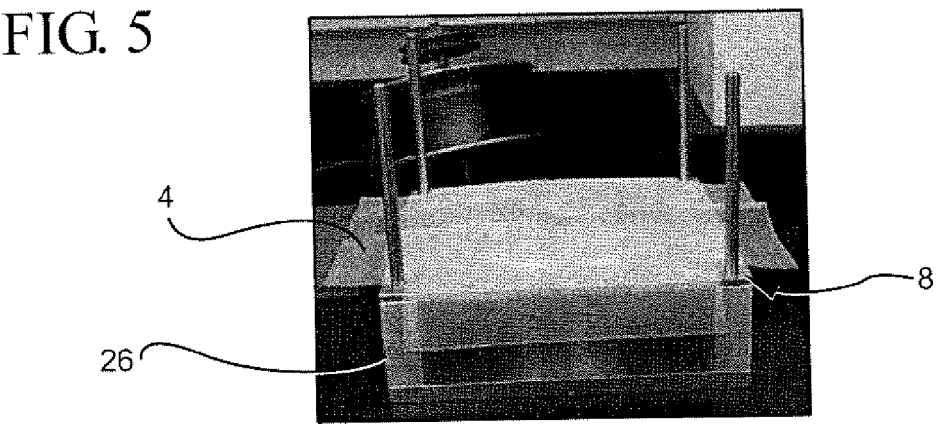
FIG. 5 is a photograph of the prosthesis forming apparatus of the present invention shown in FIGS. 1-4, and illustrating the configuration of the apparatus in a first step in the process of forming a mesh prosthetic device, and specifically showing a mesh material placed atop a mesh support plate of the apparatus.

According to one embodiment, a thermoforming apparatus 2 for forming a substantially flat polymeric fabric into a contoured or complex shape for the purpose of creating a preformed, seamless, anatomically contoured device for supporting an anatomical structure or replacement therefor is illustrated by FIGS. 1-4 of the drawings. More specifically, the present invention is used to form a polypropylene mesh 4 into a shape for supporting an anatomical structure or its replacement, such as a breast implant. FIGS. 1 and 2 show one form of the apparatus 2 constructed in accordance with the present invention in semi-exploded, isometric views. FIG. 3 shows a side view of the apparatus 2 in an open configuration. FIG. 4 shows a front view of the apparatus 2 in a closed configuration.

Initially referring to FIGS. 1-4 of the drawings, it will be seen that apparatus 2 for making such a support device 6 includes a support plate 8 made from a thermally conductive material. The support plate 8 includes a first opening 10 formed through the thickness thereof, which is preferably centrally located on the support plate 8. This first opening 10 has a predetermined shape.

The apparatus 2 also includes an ironing plate 12 made from a thermally conductive material. The ironing plate 12 has a second opening 14 formed through the thickness thereof, which also has a predetermined shape. The shape of the second opening 14 formed in the ironing plate 12 is the same as or similar to the shape of the first opening 10 formed in the support plate 8. The second opening 14 in the ironing plate 12 is also centrally located so that it is in alignment with the first opening 10 formed in the support plate 8 when the ironing plate 12 is placed on top of the support plate 8.

The apparatus 2 also includes a core plate 16 which is also made from a thermally conductive material. The core plate 16 has a lower surface 18 and a core 20 extending outwardly from the lower surface 18 thereof. The core 20 has a predetermined male form, and is at least partially received by and extends through the second opening 14 of the ironing plate 12 and the first opening 10 of the support plate 8 when the core plate 16 is placed on top of the ironing plate 12. The core 20 defines the shape that is imparted to the mesh support device 6.

As mentioned previously, the support plate 8, ironing plate 12 and core plate 16 are preferably formed from a thermally conductive material, and this material may be steel or aluminum, for example. Also, the ironing plate 12 and the core plate 16 are relatively heavy in that, when the ironing plate 12 is placed on the support plate 8, it can hold in position a sheet of mesh material 4 between the support plate 8 and the ironing plate 12 by its shear weight. The core plate 16 also, by its shear weight, when placed on top of the ironing plate 12, will deform a portion 50 of the mesh material 4 sandwiched between the support plate 8 and the ironing plate 12 through the first and second openings 10, 14 in the support plate 8 and the ironing plate 12, respectively, to form the support device 6.

The support plate 8 includes an upper surface 22 and a lower surface 24 situated opposite the upper surface 22. The apparatus 2 may further include a platform 26 which is situated below the support plate 8. More specifically, the lower surface 24 of the support plate 8 rests on the platform 26 and is supported thereby. The platform 26 is cubical in shape in that it defines an open space 28 below the support plate 8 for receiving at least a portion of the core 20 when the core 20 extends through the second opening 14 in the ironing plate 12 and the first opening 10 in the support plate 8.

The apparatus 2 may further include a plurality of alignment rods 30. Each of the core plate 16, ironing plate 12 and support plate 8 have a plurality of alignment holes 32 formed through the thickness thereof, preferably situated in each plate corner (there are preferably four corners for each plate), so that each alignment rod 30 is receivable by a respective alignment hole 32 formed in the core plate 16, ironing plate 12 and support plate 8. The alignment rods 30 are provided to align the core plate 16, ironing plate 12 and support plate 8 with one another in a stacked arrangement, as can be seen from FIGS. 1-4 of the drawings. Preferably, the alignment rods 30 are mounted to and extend outwardly from the platform 26. Alternatively, the support plate 8 is affixed to and forms part of the platform 26, with the alignment rods 30 being mounted to and extending from the upper surface 22 of the support plate 8 in the four corners thereof.

Also, as can be seen from FIGS. 1 and 2 of the drawings, the support plate 8 includes a raised ironing pad 34 that has a flat exposed surface 36 and a beveled edge 38. The exposed surface 36 is raised above the upper surface 22 of the support plate 8. The beveled edge 38 extends between the flat raised surface 36 of the ironing pad 34 and the upper surface 22 of the support plate 8.

Also, the ironing plate 12 includes a recess 40 formed in the lower surface 42 thereof to define a recessed surface 44 situated in the recess 40 formed therein, and preferably a beveled edge 46 extending between the recessed surface 44 and the lower surface 42 of the ironing plate 12. The beveled edge 46 of the ironing plate 12 is situated in alignment with the beveled edge 38 of the support plate 8 when the ironing plate 12 is placed on top of the support plate 8. The ironing plate 12 and the support plate 8, in combination with the ironing pad 34 of the support plate 8 and the recess 40 formed in the ironing plate 12 which receives the ironing pad 34, minimizes the formation of any pleats or folds that would otherwise form in the mesh material 4 as the mesh material 4 is conforming to the shape of the core 20 during the pressing operation.

In accordance with a method of making a seamless, anatomically contoured, prosthetic device for supporting or maintaining the position of mammalian tissue, organ or structure or a replacement therefor, such as a breast implant, and as illustrated by FIGS. 3-8 of the drawings, the apparatus 2 for forming the prosthetic device is initially pre-heated, preferably to a temperature of between about one hundred (100) degrees Celsius and two hundred (200) degrees Celsius. The pre-heated apparatus 2 will cause some shrinkage in the mesh material 4 when it is placed in the apparatus 2.

Figure 6:
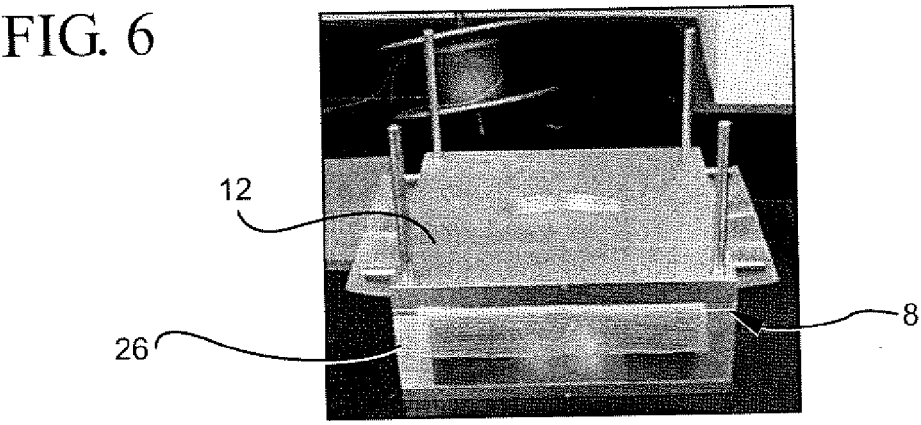
FIG. 6 is a photograph of the prosthesis forming apparatus of the present invention shown in FIGS. 1-4, and illustrating the configuration of the apparatus in a second step of the process of forming a mesh prosthetic device, and specifically showing an ironing plate of the apparatus pressing on the mesh material.
Figure 7:
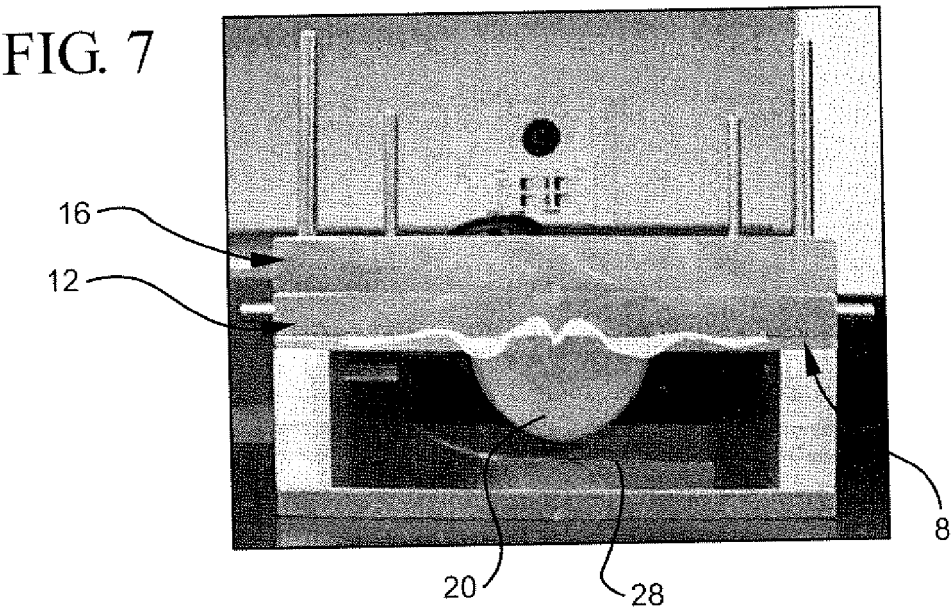
FIG. 7 is a photograph of the prosthesis forming apparatus of the present invention shown in FIGS. 1-4, and illustrating the configuration of the apparatus in a third step in the process of forming a mesh prosthetic device, and specifically showing a core plate of the apparatus penetrating the ironing plate and mesh support plate of the apparatus.
Figure 8:
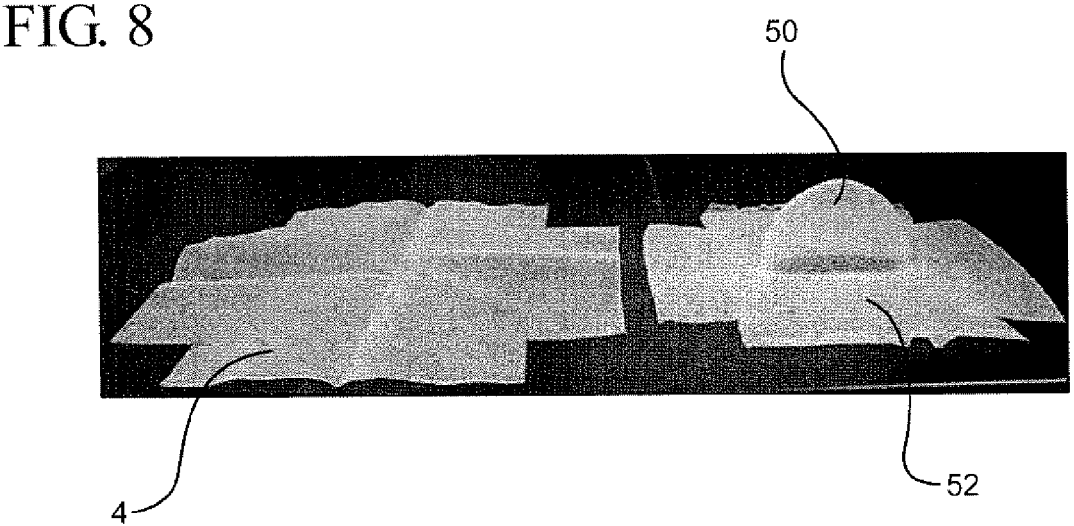
FIG. 8 is a photograph of an uncut mesh prosthetic device shaped by the apparatus of the present invention in a mesh material (shown on the right side when viewing the photograph) adjacent to the original mesh material (shown on the left side when viewing the photograph) prior to its placement on the apparatus.

The mesh material 4 is then placed on top of the support plate 8 (see FIG. 5), and the ironing plate 12 is then placed onto the mesh material 4 so that the mesh material 4 is sandwiched between the support plate 8 and the ironing plate 12 (see FIG. 6). Then, the core plate 16 is placed on top of the ironing plate 12 so that the core 20 penetrates through the ironing plate 12 and the support plate 8, and in particular the second opening 14 and the first opening 10, respectively, formed therein, and thus deforms a portion 50 of the mesh material 4 into a contoured shape that conforms to the shape of the core 20. The contoured shaped portion 50 of the mesh material 4 is surrounded by excess mesh material 52 (see FIG. 7). In this orientation, the apparatus 2 is then retained at its pre-heated temperature for between about three (3) minutes and about three (3) hours. Then, the apparatus 2 is allowed to cool preferably to room temperature, over a time period of between about three (3) minutes and about five (5) hours. The mesh material 4, containing the shaped portion 50, is removed from between the support plate 8 and the ironing plate 12. FIG. 8 shows the shaped portion 50 formed in the mesh material 4 (on the right when viewing FIG. 8) adjacent to the original mesh material 4 (on the left when viewing FIG. 8). The shaped portion 50 is then separated from the excess mesh material 52, with the separated shaped portion 50 thus formed defining the seamless, anatomically contoured, prosthetic support device 6.

Figure 9:
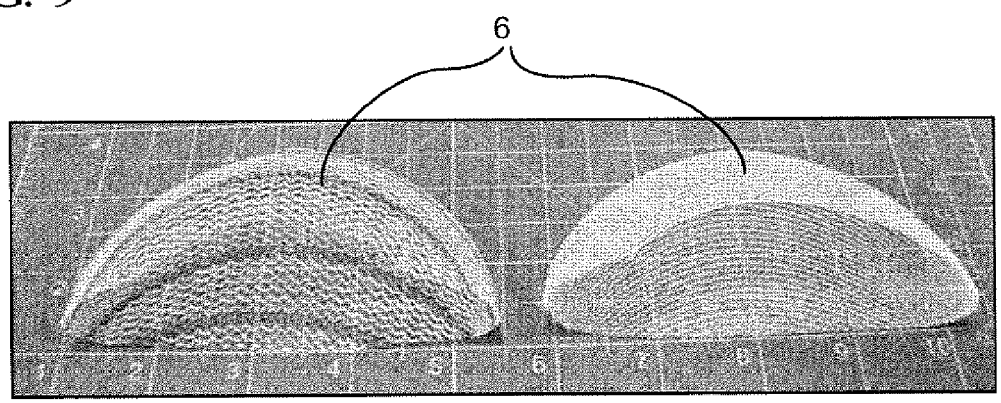
FIG. 9 is a photograph of two versions of a mesh prosthetic device forming using the method and apparatus of the present invention and using PROLENE™ mesh material (shown on the left side when viewing the photograph) and PROLENE™ Soft mesh material (shown on the right side when viewing the photograph).
Figure 10:
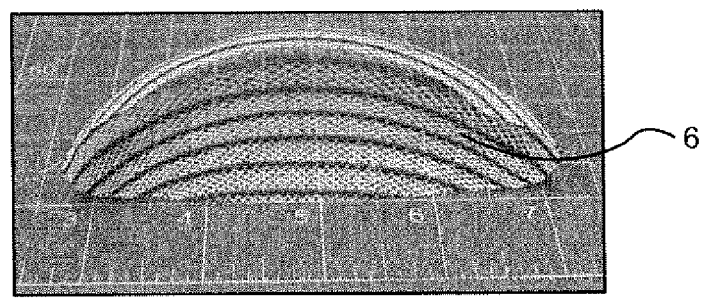
FIG. 10 is a photograph of another version of a mesh prosthetic device formed using the method and apparatus of the present invention and utilizing Ultrapro™ mesh material.

FIG. 9 shows an example of a mesh support device 6 made from a Prolene™ mesh material (on the left when viewing FIG. 9), formed in accordance with the present invention, and a support device 6 made from a Prolene™ Soft mesh material (on the right when viewing FIG. 9), also constructed in accordance with the present invention. FIG. 10 shows an example of a support device 6 made from an Ultrapro™ mesh material, a partially absorbable mesh, also constructed in accordance with the present invention.

Figure 14:
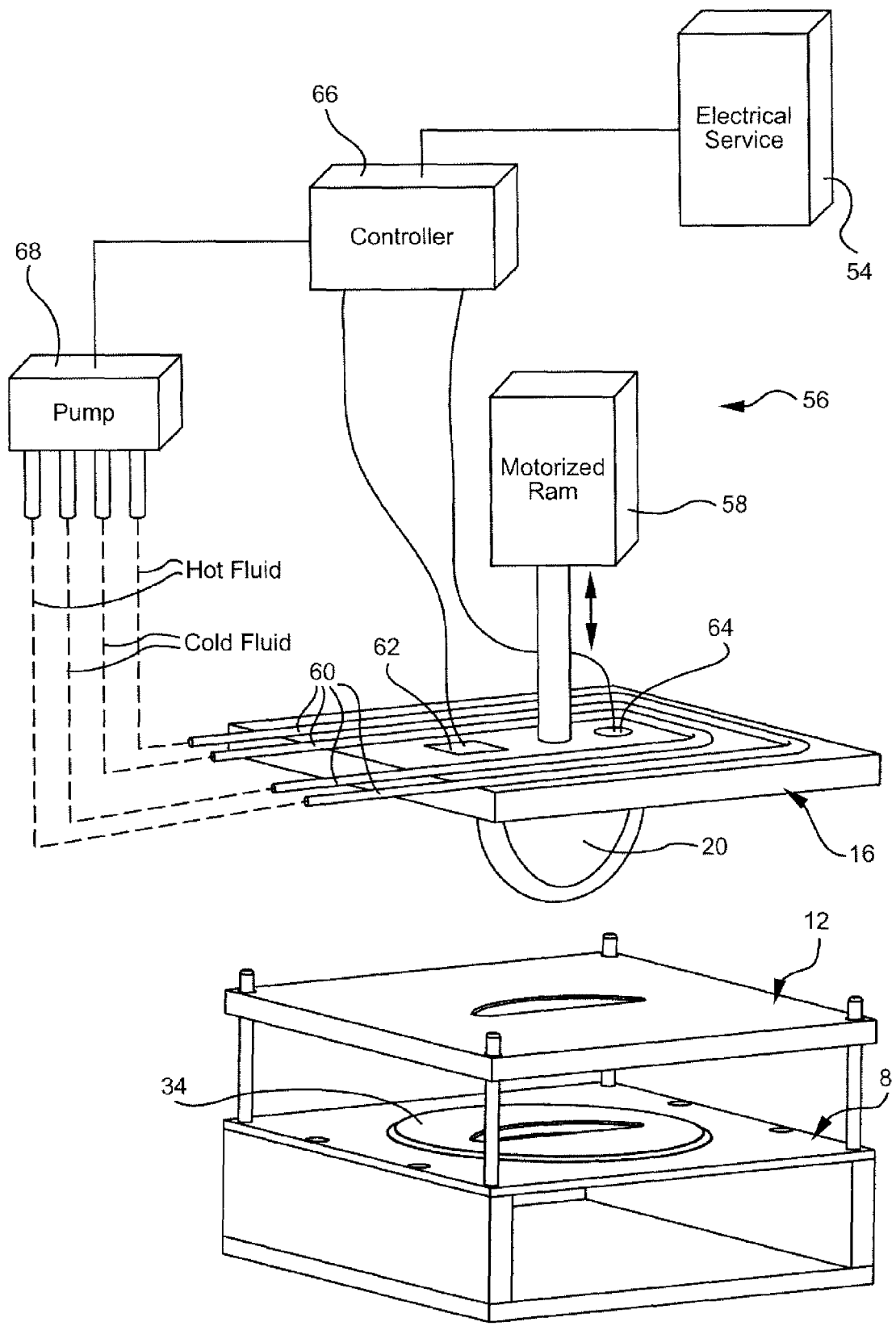
FIG. 14 is a pictorial illustration of another form of apparatus for forming a prosthetic support device constructed in accordance with the present invention.

An automated process for creating the preformed support device 6 is similar to the process described previously, except that the core plate 16 is introduced in a controlled manner, forming the contoured mesh portion 50 over a predetermined period of time, preferably between about 0.1 and about 100 centimeters/minute. In a preferred embodiment, the apparatus 56 of an automated process would also employ active means for heating the apparatus 56 (e.g. heater cartridges or equivalent) and active means for cooling the apparatus 56 (e.g cooling lines, or equivalent). An example of such an apparatus 56 for the automated manufacture of a mesh support device 6 is illustrated by FIG. 14 of the drawings.

More specifically, a motorized ram 58 that moves in an axially direction may impart a force on the core plate 16 to move the core plate 16 at a controlled speed toward the ironing plate 12 and the support plate 8, with the mesh material 4 sandwiched between the ironing plate 12 and the support plate 8. One or more of the support plate 8, ironing plate 12 and core plate 16 may include a conduit 60 which is in thermal communication (for example, mounted on or in) one or more of the plates. The conduit 60 may first carry a heated fluid to pre-heat the plate or plates to a desired temperature. Then, the same conduit 60, or a different conduit, may carry a cooling fluid or coolant, to cool the plate or plates of the apparatus 56 at a desired rate to bring the apparatus 56 down to a predetermined temperature, such as room temperature. Alternatively, the plate or plates may include electrical heating elements 62 that are used to heat the plate or plates, and then the heating elements 62 are turned off electrically and the apparatus 56 is allowed to cool either naturally, or with the aforementioned conduits 60 carrying a cooling fluid. Temperature sensors 64 may be affixed to one or more of the plates to sense the temperature of the plates, and the sensors 64 provide an electrical signal to a controller unit 66, which either controls a pump 68 which selectively pumps heated fluid or cooling fluid through the conduit 60 or conduits or a source of electricity 54 which selectively provides power to the heating elements 62, so that the temperature of the plates may be precisely controlled and monitored throughout the manufacturing process.

There are two primary reasons that the apparatus 2,56 is heated prior to introducing the mesh material 4. First, the material 4 may be shrunk in a controlled manner before it is stretched (for example, 145 degrees Celsius causes about a five percent (5%) shrinkage for polypropylene mesh), thereby allowing the mesh material 4 to become thicker before being thinned again during the stretching step. This further imparts a resiliency to the preformed support device 6 wherein the device can support at least its own weight, and can additionally support the weight of body fluids that stick to it, a feature which facilitates the use of the device significantly over a device that cannot support its own weight. Because no female cavity is used in the apparatus 2,56 of the present invention, there is no radiant heat that may serve to reduce the control of the stretching by imparting further shrinkage to the mesh 4 during the stretching step. Furthermore, use of a female cavity would have required maintaining tight dimensional tolerances and process parameters to avoid undue drag during the stretching step. By shrinking the mesh material 4 before stretching it, the strength and resiliency of the original material is retained.

The second reason the apparatus 2,56 of the present invention is preferably heated prior to introducing the mesh material 4 is to increase the compliancy of the mesh 4 being formed in order to minimize creation of pleats and folds. A compliant mesh 4 between the hot plates cannot form pleats or folds as it is being formed because the hot plates, with their ironing features, prohibit the formation of pleats and folds. The ironing features of the apparatus 2,56, including the raised ironing pad 34 of the support plate 8 and the recessed surface 44 of the ironing plate 12, and preferably in conjunction with the beveled edges of each plate 38,46, do not actually iron out any pleats or folds; rather, they prevent them from forming in the first place. It is interesting to note that if the process is performed without pre-heating the apparatus 2,56, or without a sufficient normal force applied to the mesh material 4, pleats and folds may form and possibly can actually lift the ironing plate 12 as the core 20 is introduced into the mesh material 4 before the mesh material 4 begins to rip and tear.

Figure 11:
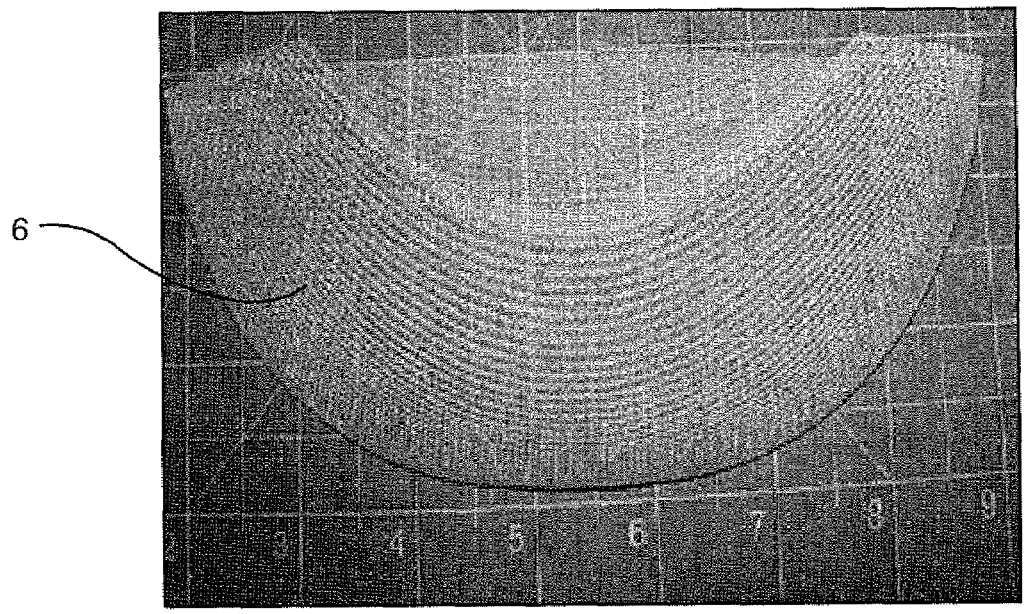
FIG. 11 is a photograph of a version of a mesh prosthetic device formed using the method and apparatus of the present invention, the prosthetic device having a bottom portion formed with a canoe shape.
Figure 12:
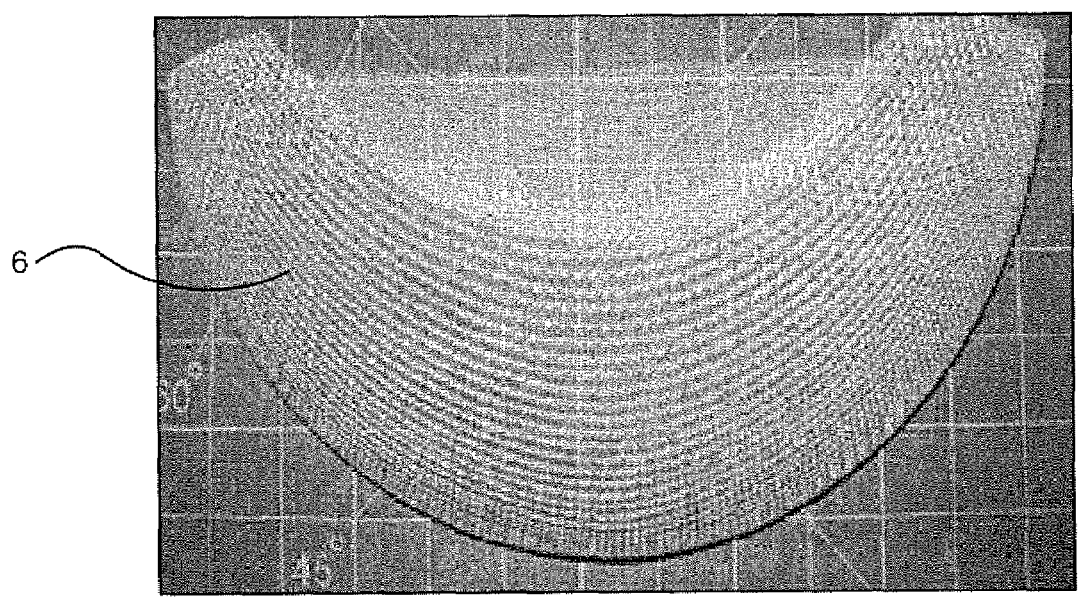
FIG. 12 is a photograph of a version of a mesh prosthetic device formed as using the method and apparatus of the present invention, the prosthetic device having a bottom portion formed with a rounded shape.

The process and apparatus of the present invention further enable formation of a preformed support device 6 from a flat mesh material 4 having a uniquely large surface area to cavity opening area ratio that is free from pleats and folds. A unique effect of creating a preformed support device 6 from a flat mesh 4 is that the resulting preformed support device 6 has curved or contoured wales and pores that gradually taper in size. Various sizes and shapes of preformed support devices 6 have been fabricated. Examples of a prosthetic device approximately seventeen (17) centimeters wide and about seven (7) centimeters deep and having a canoe-shaped bottom, and a prosthetic device approximately fourteen (14) centimeters wide and about seven (7) centimeters deep and having a round bottom are shown in FIGS. 11 and 12, respectively. An upper limit on the surface area to cavity opening area ratio has not yet been determined, but the inventors hypothesize that the upper limit can be extremely large, at least on the order of twenty to one.

Figure 13A:
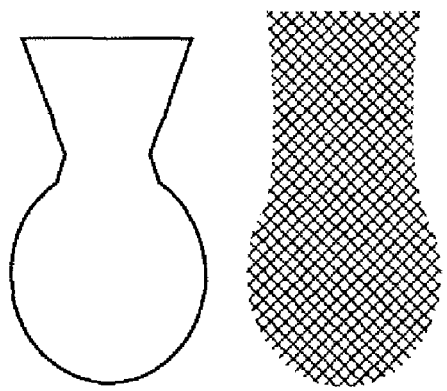
FIGS. 13A and 13B are pictorial illustrations of the apparatus of the present invention forming a desired shape in a mesh material, and illustrating several steps in the method of forming a mesh prosthetic device in accordance with the present invention.
Figure 13B:
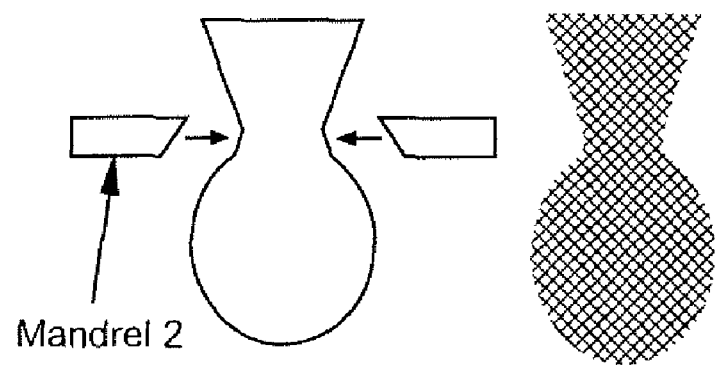

The process of the present invention may also be used to create preformed support devices 6 in complex configurations. For example, a mushroom-shaped preformed support device, shaped as an ellipsoid located underneath a frustum of a cone, underneath another frustum of a cone, may be fabricated. The method and apparatus for forming such a device would include the method and apparatus described above, but with at least one extra step. For example, more than one stretching step may be employed. By way of example, the steps for forming such a preformed support device are shown in FIGS. 13A and 13B. More specifically, and as shown in FIGS. 13A and 13B, a first mandrel having the desired shaped is used alone to form the mesh into an approximate shape (see FIG. 13A). A second mandrel is then used to refine the shape of the support device (see FIG. 13B). In theory, any number of forming steps could be employed to make preformed support devices having very complex shapes.

Thus, in accordance with the present invention and as described previously, a preformed support device 6 may be fabricated from a mesh material 4 having substantially the same cross-section, strength and resilience as the raw mesh material. The preformed support device 6 formed in accordance with the present invention also has sufficient resiliency to support at least its own weight when placed on almost any surface and in almost any orientation.

Furthermore, a preformed support device 6, constructed in accordance with the present invention, has sufficient resiliency to withstand deforming when body fluids stick to it. The preformed support device 6 formed in accordance with the present invention also has a large surface area to cavity opening area ratio that is seamless and free from folds and pleats. The support device 6 having cut-away and removed portions is particularly adapted to facilitate securing the mesh to tissue or muscle surrounding natural breast tissue or a breast implant.

The preformed support device 6 constructed in accordance with the present invention may be fabricated from a mesh material 4 having a controlled porosity gradient, and may be further formed into complex configurations, for example, with a center portion that is necked thinner than the top or bottom portion, as shown in FIGS. 13A and 13B. The support device 6 having such a curved or complex configuration does not need to be fabricated by hand or by complex and expensive equipment.

The preformed support device 6, constructed in accordance with the apparatus of the present invention and method disclosed herein, may have a configuration nominally comprised of various combinations of essentially geometric shapes including ellipsoids (and segments thereof), spheroids (and segments or sectors thereof), prisms (and segments thereof), pyramids (and frustums thereof), cones (and segments and frustums thereof), cylinders (and segments and frustums thereof), wedges (and segments thereof), paraboloids (and segments thereof), hyperboloids (and segments thereof) and other geometric shapes.

The apparatus 2,56 of the present invention does not have a female cavity, and this enables a more uniform forming step. Also, the apparatus 2,56 with its ironing plate 12 and support plate 8, and raised ironing pad 34 and recessed surface 44 that receives the ironing pad 34, and the beveled edges 38,46 formed in each of the support plate 8 and the ironing plate 12, minimize any possibility of the formation of pleats and folds when the apparatus 2,56 and the mesh material 4 are heated.

The method of the present invention utilizes a shrinking and stretching step to allow the creation of a preformed support device 6 having substantially the same cross-section, strength and resilience as the input material. Having such a preformed support device formed in accordance with the present invention can reduce the duration of a given surgical procedure, because there is no need for a surgeon to form a flat mesh into a formed mesh support during the procedure. Also, having a preformed support device 6 can minimize the amount of dust introduced into the sterile field when creating a formed support device during a surgical procedure.

The contoured and curved wales and gradual changes in porosity may be incorporated into a prosthetic support device 6 formed from a flat mesh sheet 4 in accordance with the method of the present invention and with the apparatus 2,56 of the present invention. Knitting a three dimensional mesh material into a support device, as is conventionally done, yields only linear wales and a uniform porosity. Also, with the present invention, a unique surface ornamentation may be formed in the support device constructed in accordance with the present invention, such as gradually changing pore sizes and/or stripes, as can be found in the preformed support device of the present invention shown in FIG. 10 of the drawings.

Figure 15:
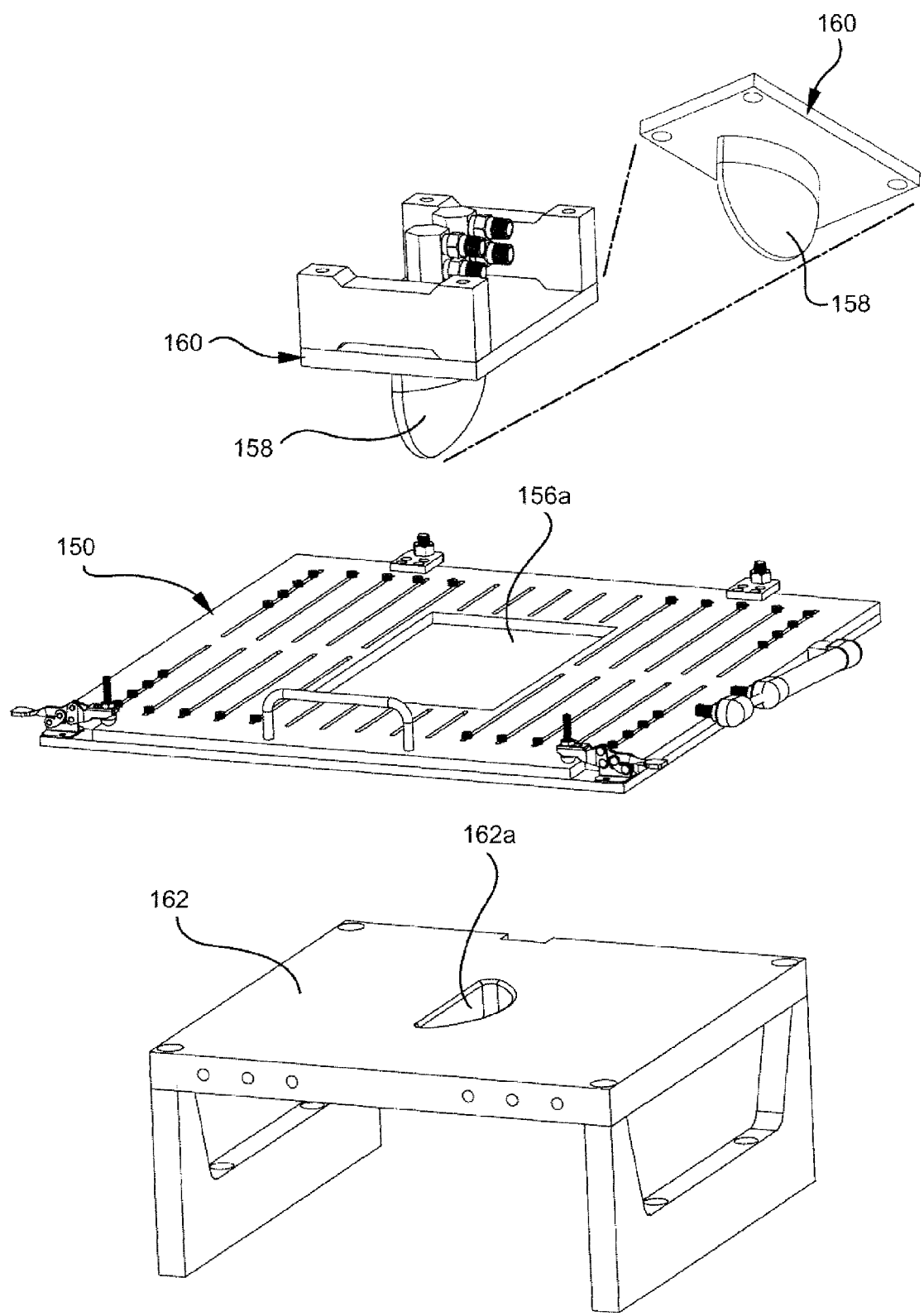
FIG. 15 illustrates one embodiment of the apparatus of the present invention including a clamping plate.
Figure 16A:
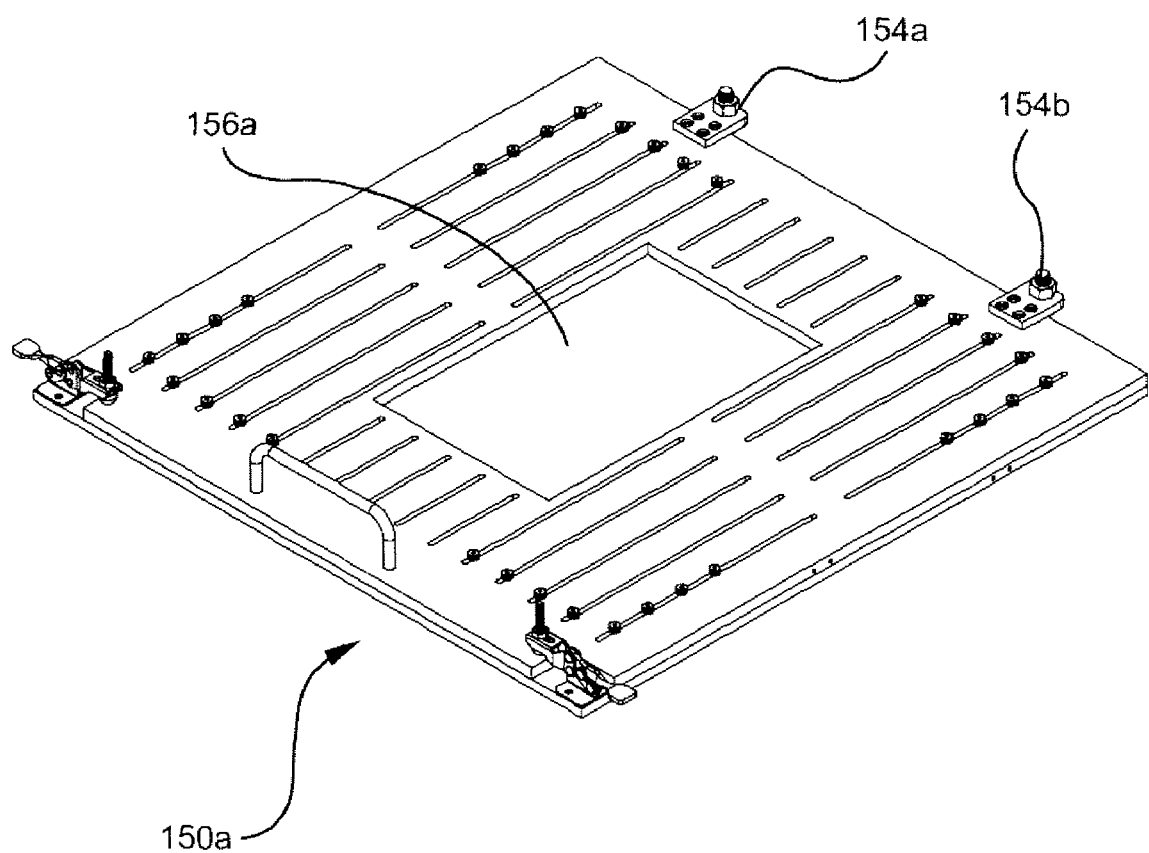
FIGS. 16a,b illustrates detail of the clamping plate shown in FIG. 15.
Figure 16B:
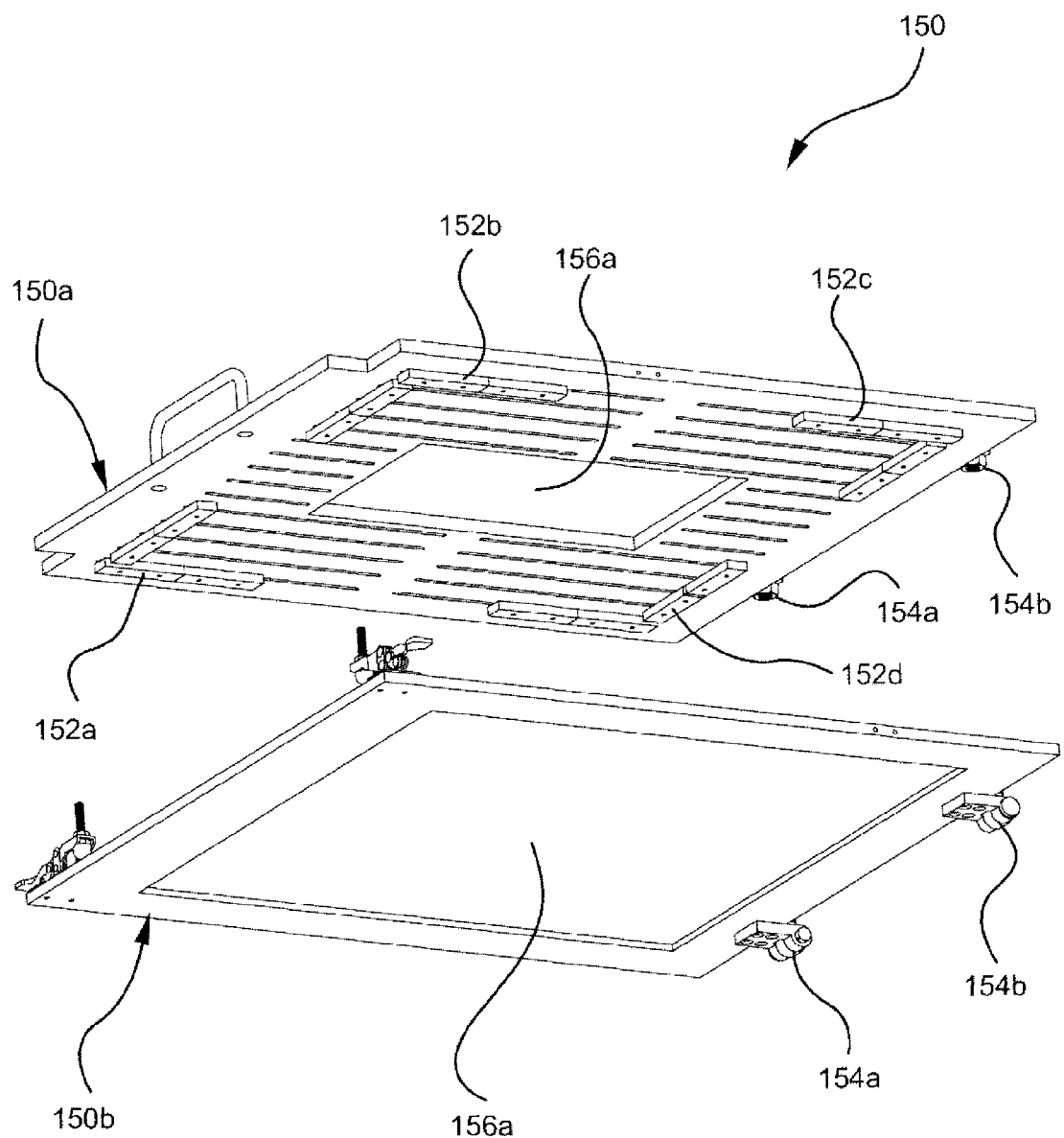

In an alternate embodiment, the above-described apparatus and method is similar, but with a simple, discrete clamping component or clamping plate used in place of the heated ironing plate. The clamping plate is best illustrated in FIGS. 15, 16a, and 16b. The discrete clamping plate 150 is made from a rigid material and having two layers 150a and 150b that are pivotally joined to each other with hinges 154a and 154b. The surface of layer 150a that faces layer 150b has discrete gripping elements 152a, 152b, 152c, 152d that can grasp, clamp, or otherwise securely hold in place predetermined discrete locations of the mesh when the clamping plate is closed and in contact with the support plate 162. In the present embodiment the gripping elements are substantially located at the four corners of the clamping plate layer 150a but positioned such that when the two clamping layers 150a and 150b are closed upon each other, the gripping elements are positioned within the opening 156b of layer 150b. In addition clamping plate layer 150a may have at least four other fastening devices that serve as a way to hold the mesh to the layer 150a before the layer 150b is closed upon layer 150a to secure the mesh between the two layers 150a and 150b. The discrete gripping elements 152a, 152b, 152c, 152d allow clamping of portions of the margins of the mesh against support plate 162, leaving other portions of the mesh unclamped so that the mesh is better able to shrink when heated or move when stretched during the forming process. The grippers may be positioned in a number of configurations for different size products. Preferably, the grippers are located so that at least 20% or more of the outer margins of the mesh remain unclamped. As with the embodiments described above, the clamping plate includes centrally located openings 156a and 156b and the support plate has an opening 162a through which the core 158 of the core plate 160 passes.

In this embodiment, the core and core plate are made from a thermally conductive material with a predetermined three-dimensional male shape, that is preferably at least 40 mm in depth The core plate may have built in cooling and heating elements attached to and driven by an actuator.

A preferred process for making an implant using this apparatus involves pre-heating the support plate 162 to an elevated temperature above the softening point at which the mesh can shrink or deform. The mesh is then clamped in place between the clamping plate 150 and support plate 162 using the gripping elements 152a, 152b, 152c, 152d of the clamping plate. The grippers firmly hold the mesh against the preheated support plate 162. The mesh is held in contact with the support plate 162 for at least five seconds at an elevated temperature above the softening point of the mesh.

The core plate 160 has also been pre-heated to a forming temperature that is above the pre-heated temperature of the support plate 162 but below the melting temperature of the mesh material. The heated core plate 160 is then moved into place in a controlled manner to thereby stretch the mesh into the predetermined three-dimensional configuration. The core plate 160 preferably remains in place for 1-10 minutes, and more preferably between 2 and 5 minutes, to anneal and heat-set the mesh to the desired shape.

Following heat-setting of the mesh, the formed mesh is quenched by cooling the core plate 160 to a lower temperature, at or below which the formed mesh shape will no longer change upon removal of the core plate 160. The core plate 160 is then separated and the mesh removed from the core plate 160, at which time the excess mesh can be cut away.

Figure 17:
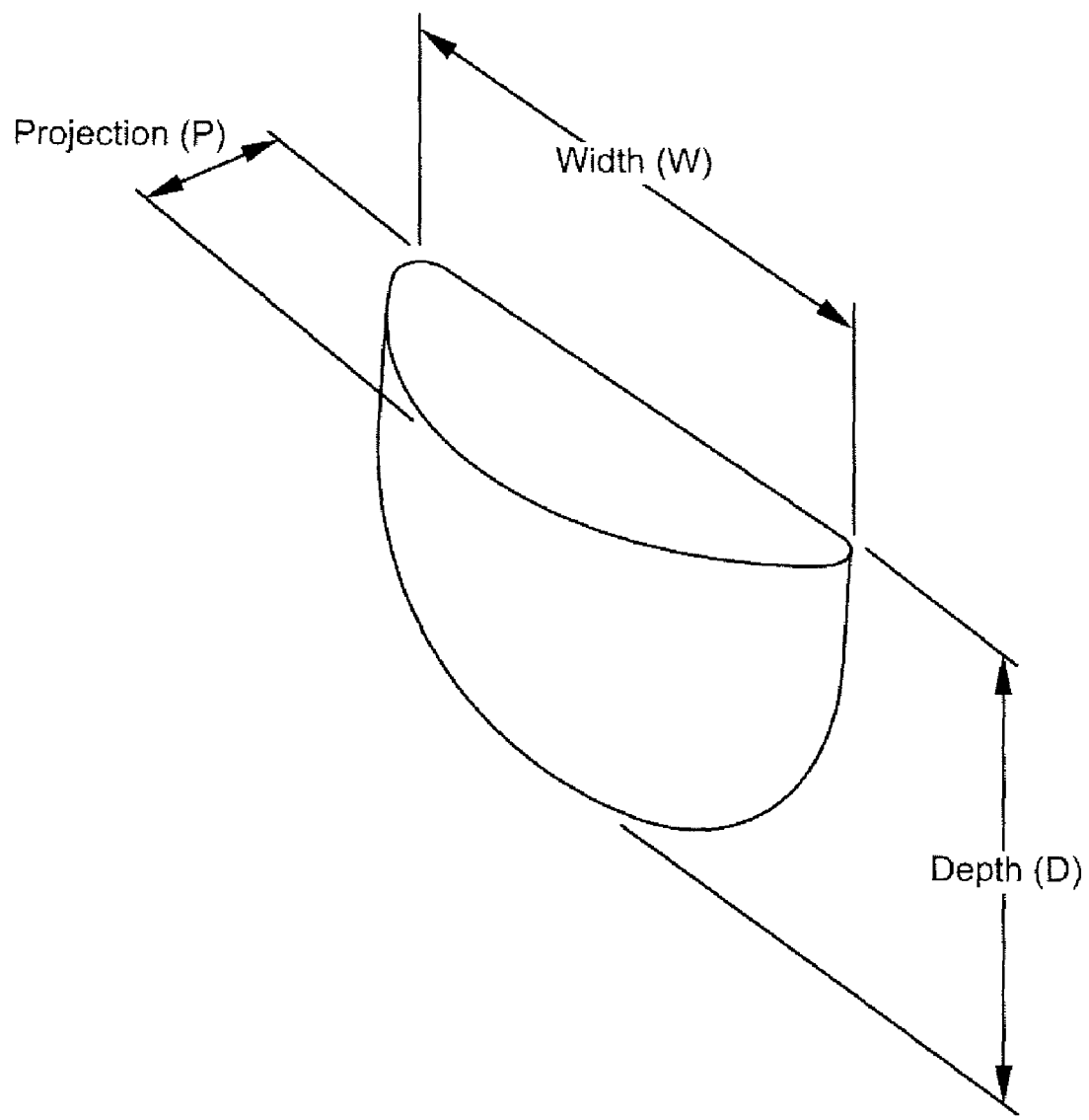
FIG. 17 illustrates dimensional terminology.

The following are preformed mesh dimensions and process parameters associated with the formation of four different preformed polypropylene mesh devices made from PROLENE™ mesh material or PROLENE™ soft mesh material. FIG. 17 illustrates the dimensions set forth below.

Examples of Mandrel (Core Plate) Dimensions

| Examples of Mandrel (Core Plate) Dimensions | | | | |
|---|---|---|---|---|
| Width (cm) | Projection (cm) | Depth (cm) | D/P ratio | D/W Ratio |
| 10 | 3.6 | 6.0 | 1.7 | 0.6 |
| 12 | 3.8 | 8.5 | 2.2 | 0.7 |
| 14 | 4.2 | 9.5 | 2.3 | 0.7 |
| 17 | 5.0 | 11.0 | 2.2 | 0.6 |

The following are ranges of the above parameters that temperatures and core press forming speeds that are suitable for use in fabricating preformed polypropylene mesh implants.

| Hot Press Thermal Forming Parameters for Propylene Mesh | | | | | | | |
|---|---|---|---|---|---|---|---|
| | Temperature | | | Time | | Mandrel | |
| | Mandrel | | Cooling/Conditioning | | | Forming | |
| Preferred Range | Forming Temp (C.) | Plate Temp (C.) | Temp. (C.) | Preheat Time (s) | Forming Time (s) | Quenching Time (s) | Velocity (cm/min) | Mesh Type |
| Low | 130 | 110 | 80 | 5 | 10 | 120 | 30 | |
| High | 176 | 140 | 100 | 300 | 600 | 600 | 390 | |
| Most Preferred | 155 | 135 | 80 | 60 | 180 | 200 | 180 | |
| Examples: | 165 | 140 | 80 | 60 | 180 | 200 | 180 | PROLENE Mesh |

| Dimensions of The Mandrel used: | | | | |
|---|---|---|---|---|
| Width (cm) | Projection (cm) | Depth (cm) | D/P ratio | D/W Ratio |
| 17 | 5.0 | 11.0 | 2.2 | 0.6 |

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method of making a seamless, anatomically contoured, implantable prosthetic device for implantation within a human patient to support or maintain the position of tissue, an organ or structure or a replacement therefor, which comprises the steps of:

pre-heating an apparatus for forming the prosthetic device, the apparatus including a support plate made from a thermally conductive material and having a first opening formed through the thickness thereof and a lower surface substantially free from contact with any other surface, the first opening having a predetermined shape, an ironing plate made from a thermally conductive material and having a second opening formed through the thickness thereof, the second opening having a predetermined shape which is as least one of the same as and similar to the predetermined shape of the first opening formed in the support plate, and a core plate made from a thermally conductive material and having a lower surface and a core extending outwardly from the lower surface thereof, the core having a predetermined male form, the core being at least partially receivable by and extending through the second opening of the ironing plate and the first opening of the support plate, wherein the apparatus does not use or otherwise incorporate a female mold cavity;

placing an implantable, biocompatible mesh material on top of the support plate;

placing the ironing plate onto the mesh material so that the mesh material is sandwiched between the support plate and the ironing plate;

shrinking the mesh material between the heated support plate and ironing plate;

following the shrinking step, placing the core plate on top of the ironing plate so that the core penetrates through the ironing plate and the support plate and deforms a portion of the mesh material into a contoured shaped portion which is surrounded by excess mesh material, wherein the lower surface of the core plate and associated contoured shaped mesh portion is openly exposed;

removing the mesh material containing the contoured shaped portion from between the support plate and the ironing plate; and separating the shaped portion from the excess mesh material, the separated shaped portion defining the seamless, anatomically contoured, prosthetic device.

2. A method as defined by claim 1, wherein the step of pre-heating the apparatus includes the step of pre-heating the apparatus to a temperature of between about one hundred degrees Celsius and about two hundred degrees Celsius.

3. A method as defined by claim 1, wherein after the step of placing the core plate on top of the ironing plate so that the core penetrates through the ironing plate and the support plate and deforms a portion of the mesh material into a contoured shaped portion, the method further comprises the step of maintaining the temperature of the apparatus for a predetermined period of time.

4. A method as defined by claim 3, wherein the step of maintaining the temperature of the apparatus for a predetermined period of time includes the step of maintaining the temperature of the apparatus for a predetermined period of time from about three minutes to about three hours.

5. A method as defined by claim 3, wherein after the step of maintaining the temperature of the apparatus for a predetermined period of time, the method further comprises the step of allowing the apparatus to cool for a predetermined period of time.

6. A method as defined by claim 5, wherein the step of allowing the apparatus to cool for a predetermined period of time includes the step of allowing the apparatus to cool for a predetermined period of time of between about three minutes and about five hours.

* * * * *